US005676742A

United States Patent [19]
Arendt et al.

[11] Patent Number: 5,676,742
[45] Date of Patent: Oct. 14, 1997

[54] MONO AND DIBENZOATE ESTER BLENDS AS CAULK PLASTICIZERS THAT ARE BIORESISTANT TO FUNGAL GROWTH

[75] Inventors: William D. Arendt, Libertyville; David Wayne Barrington, Park Ridge, both of Ill.

[73] Assignee: Velsicol Chemical Corporation, Rosemont, Ill.

[21] Appl. No.: 550,526

[22] Filed: Oct. 30, 1995

[51] Int. Cl.$^6$ .............. C08K 5/10; A01N 31/00; C09G 1/00; C09J 133/08
[52] U.S. Cl. .............. 106/15.05; 106/3; 106/287.26; 514/129; 514/143; 514/148; 523/122; 524/291; 524/292; 524/765
[58] Field of Search .............. 106/3, 15.05, 287.26; 523/122; 524/291, 292, 765; 514/129, 143, 148

[56] References Cited

U.S. PATENT DOCUMENTS

| | | | |
|---|---|---|---|
| 3,785,860 | 1/1974 | Zdanowski | 106/8 |
| 4,024,164 | 5/1977 | Bailey et al. | 549/484 |
| 4,070,510 | 1/1978 | Kahn | 106/10 |
| 4,071,645 | 1/1978 | Kahn | 106/10 |
| 4,074,058 | 2/1978 | Bailey et al. | 560/105 |
| 4,107,192 | 8/1978 | Bailey et al. | 554/121 |
| 4,277,387 | 7/1981 | Jordan, Jr. et al. | 524/292 |
| 5,216,057 | 6/1993 | Pratt et al. | 524/269 |
| 5,422,001 | 6/1995 | Jones et al. | 524/292 |
| 5,494,947 | 2/1996 | Kaplan | 523/122 |
| 5,527,845 | 6/1996 | Strelow et al. | 524/271 |
| 5,532,300 | 7/1996 | Koubek et al. | 524/47 |

*Primary Examiner*—Anthony Green
*Attorney, Agent, or Firm*—Sidley & Austin

[57] ABSTRACT

The present invention comprises dipropylene glycol dibenzoate and diethylene glycol dibenzoate, the improvement comprising the addition of dipropylene glycol monobenzoate or diethylene glycol monobenzoate, whereby the plasticizer is resistant to fungal growth.

12 Claims, No Drawings

MONO AND DIBENZOATE ESTER BLENDS AS CAULK PLASTICIZERS THAT ARE BIORESISTANT TO FUNGAL GROWTH

BACKGROUND OF THE INVENTION

This invention relates to new mono and dibenzoate ester blends that can be used as caulk plasticizers. In particular, this invention relates to new ester blends that are unexpectedly more bioresistant to fungal growth than dibenzoates. Still another object to the present invention is the creation of plasticizers having good compatibility with various resinous materials.

Other objects of the present invention will become apparent from the ensuing description.

SUMMARY OF THE INVENTION

Dipropylene glycol dibenzoate and diethylene glycol dibenzoate have each been used as plasticizers for latex caulks. However, caulks containing these dibenzoates are more prone to fungal growth than caulks based on plasticizers such as butyl benzyl phthalate. New plasticizers have now been discovered that have surprisingly good resistance to fungal growth. More specifically, one new plasticizer that has now been discovered comprises dipropylene glycol dibenzoate and high levels of dipropylene glycol monobenzoate. Another new plasticizer that has now been discovered comprises diethylene glycol dibenzoate with high levels of diethylene glycol monobenzoate. Thus, it has now been discovered that the addition of a particular monobenzoate to a particular dibenzoate surprisingly resulted in a plasticizer that was more resistant to fungal growth than the corresponding dibenzoate alone. These new plasticizers were tested in caulks and were found to have good performance in latex caulk formulations. A blend of the dipropylene glycol mono and dibenzoate blend and the diethylene glycol mono and dibenzoate blend is also more fungal resistant than the dibenzoate only blend and functions well in latex caulks. Based on the performance of these high hydroxyl benzoate blends, it is likely that they will perform in other latex systems such as polyvinyl acetate adhesive systems and in water based coatings as plasticizers and/or coalescents. Use in general plasticizers formulations based on other formulations are envisioned.

DETAILED DESCRIPTION OF THE PREFERRED EMBODIMENTS

Below are the preferred embodiments of the present invention.

Dipropylene glycol dibenzoate:

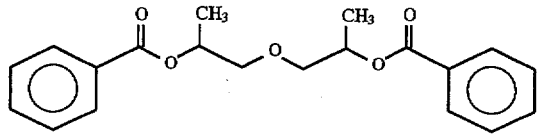

Dipropylene glycol monobenzoate:

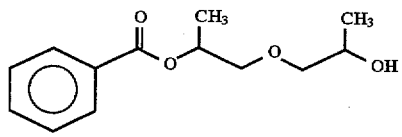

Diethylene glycol dibenzoate:

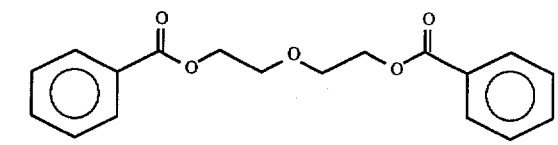

Diethylene glycol monobenzoate:

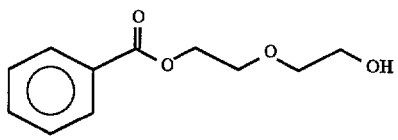

The foregoing embodiments of the present invention demonstrate that there are amounts of dipropylene glycol monobenzoate and diethylene glycol monobenzoate that are suitable to reduce fungal growth with dibenzoate plasticizers. Further, blends of all four plasticizers, e.g. a 50/50 blend of dipropylene glycol mono and dibenzoate with diethylene glycol mono and dibenzoate, also reduce fungal growth as opposed to a 50/50 blend of the dibenzoates alone. The embodiment including diethylene glycol monobenzoate in the plasticizer is believed to be the preferred embodiment.

Typically it is desired that the plasticizer used be fully esterified and partially esterified plasticizers are considered not acceptable for many applications. The DPG monobenzoate and DEG monobenzoate blended with dibenzoates were found surprisingly to function acceptably as latex caulk plasticizers.

Further, the exterior exposure data on the DPGB and DEGB and the blend demonstrate that benzoates blends (with the monobenzoates) outperform typical prior art plasticizers, e.g. butyl benzyl phthalate.

EXAMPLE 1

Neat Biological Growth Resistant of Benzoate Blends

Benzoic acid and dipropylene glycol were placed in a reactor to make plasticizer esters. Samples of plasticizer esters were collected at various intervals during the reaction cycle so that the hydroxyl content of the finished ester would be varied from the normal hydroxyl value of about fifteen upwards to over fifty. Three different samples of the finished ester were collected, each having a different hydroxyl value: (i) high; (ii) medium; and (iii) low (normal for the dibenzoate). Thus, the higher the percentage of dipropylene glycol monobenzoate, the higher the hydroxyl value.

The same procedure was then repeated with benzoic acid and diethylene glycol.

Thus, a total of six different samples of esters were taken at various reaction intervals during typical preparation of dipropylene glycol dibenozoate and diethylene glycol dibenzoate. These samples were then finished in a typical manner by neutralizing any remaining benzoic acid with soda ash, water washing and drying. After these steps, the samples were then analyzed for hydroxyl content using wet chemistry.

The hydroxyl values ranged from twelve to forty-five. See Table 1.

Using the high, medium and low hydroxyl value samples of dipropylene glycol dibenzoate and diethylene glycol dibenzoate corresponding high, medium and low hydroxyl value 50/50 blend was prepared by blending the two esters together. The hydroxyl values of the blended material was determined in the same manner as the other samples. The hydroxyl value range of the 50/50 blend was from twelve to fifty eight.

These nine samples, along with a sample of butyl benzyl phthalate, e.g. Santicizer® 160 (made by Monsanto Chemical Corporation) as a bench mark control, were sent to an independent laboratory (Biosan Laboratories, Inc. of Ferndale, Mich.) for testing to determine resistance to fungal growth by ASTMG-21.

The results of this testing showed that by increasing the amount of half ester present in the finished ester, i.e. increasing the hydroxyl value, the resulting plasticizer was more resistant to fungal attack. See Table 2.

The G-21 test was also conducted on non-nutrient agar, but the data were not definite.

For comparison of the effect of the hydroxyl content of the dibenzoates blends, a series of DPhB samples were prepared with benzoic acid added. Benzoic acid is used as a food preservative. Benzoic acid surprisingly does not retard biological growth. See Table 3.

These results were sufficient to warrant that the high hydroxyl plasticizers be evaluated in actual latex caulk formulations.

EXAMPLE 2

Performance of the Benzoate Blends in Acrylic Caulks

Table 4 lists the identifications of the plasticizer used in the caulk testing.

a. Compatibility

For a plasticizer to function in a caulk, it must be compatible with the polymeric binder. The compatibility of the plasticizers were evaluated in two different ways. A dried film of a blend of plasticizer and base emulsion was observed for film clarity and tackiness. Viscosity response of the plasticizer/polymer blend was also assessed.

A compatible plasticizer will result in a dried film that is clear and free of exudation. The dried film will also be quite tacky with a compatible plasticizer.

A plasticizer that is compatible will effect the emulsion viscosity more, making it more viscous, than a plasticizer that is incompatible.

Each plasticizer of Table 4 was mixed with RHOPLEX® 1785 (an acrylic emulsion made by Rohm & Haas, of Philadelphia, Pa.) and TRITON® X-405 (a non-ionic surfactant made by Rohm & Haas) according to Table 5. In this way, all of the plasticizers could then be tested for compatibility with a base emulsion. All of the films were clear and free of exudation, and were all very tacky as well. Then, the viscosity of each of those each mixtures was analyzed, after one hour and then at twenty-four hours. The results of this testing is shown in Table 6.

The viscosity response of the plasticizer/polymer blends indicates that the higher the hydroxyl value, the less the viscosity was increased, but the response was acceptable. The viscosity response observed with butyl benzyl phthalate was comparable to the response of low hydroxyl value plasticizers.

b. Caulk Preparation

Actual caulks were prepared using the plasticizers made in Example 1 above. These caulks were made according to the amounts shown in Table 7. To make these caulks, a low speed, high shear mixer was used.

The evaluation of plasticizer in caulk consisted of physical testing of caulks and the measurement of package stability and handling characteristics. Caulks for the evaluation were based upon a formulation recommended by the resin manufacturer for a premium quality caulk. Plasticizers were used with three different levels of hydroxyl values: (1) high; (2) medium; and (3) low, from each of the three plasticizer types, i.e., dipropylene glycol dibenzoate, diethylene glycol dibenzoate, and the 50/50 blend of dipropylene glycol dibenzoate and diethylene glycol dibenzoate. Butyl benzyl phthalate was also included as a bench mark control for comparison.

c. Wet Caulk Stability and Handling Characteristics

The stability of the caulks made herein were measured by a Semco gun (made by Semco Sales and Service, Inc. of Los Angeles, Calif.). The Semco gun is used for the rate of extrusion of a caulk after being stored at specified conditions. The storage conditions are detailed as follows: 1) Room temperature for 28 days; 2) 50° C. for 28 days; 3) after three cycles of freezing and thawing.

Initially, the medium hydroxyl value plasticizers seemed to have an advantage over the other plasticizers used, as higher rates of extrusion were observed for these plasticizers than for the high or low plasticizers in the "one" day test at room temperature ("RT"). However, as the aging process proceeded, this advantage waned. After one week and four weeks, all of the caulks were getting close to being equal in terms of stability.

The ratio of the four week data to the initial data indicates that the caulks are stable with ratios near one.

The freeze/thaw cycles or elevated temperature storage had little effect on the extrusion rates of the caulks, as can be seen by the ratios of this data to the one week data. With the exception of the low hydroxyl diethylene glycol dibenzoate, which did not make three freeze/thaw cycles.

The actual results of the Semco gun test are listed in Table 8. The freeze/thaw test was performed in accordance with the following method: (1) freeze for 16 hours at −20° F.; (2) thaw for 8 hours at room temperature; (3) repeat steps 1 and 2 twice; and (4) measure viscosity after the last thaw. The Semco gun viscosity test was performed in accordance with ASTM C-731.

d. 180° Peel Adhesion Test Data

The adhesion characteristics of the cured caulks are considered a primary indicator of caulk performance. Aluminum, glass and wood substrates were used for specific adhesion because they are all common building materials where caulk is likely to be applied. Table 9 lists the results of 180 degree peel testing on each of the substrates and the means by which the caulks failed. This "adhesion" test was performed according to the test procedure of Union Carbide as described below. Actual caulks prepared according to Table 7 using the plasticizers of Table I were tested.

Union Carbide's test procedure for determination of 180 degree peel adhesion was utilized. Listed below is the procedure as it appears in Union Carbide's bulletin, "UCAR Latexes for Water-Based Caulks and Sealants", F-44858, 11/74-5M. (7)

1. Equipment a. "Instron" Tensile Tester b. Aluminum mold (6" long×1" wide×0.025" thickness)

c. Substrates free of foreign particles.

d. 1" strip of desized, grade A airplane fabric (4.2 oz. per yard, 80/84 thread count).

e. Broadknife or spatula, and razor blade.

Procedure a. The aluminum mold is placed on the substrate in such a manner that one end of the substrate will fit into the jaws of the "Istron" Tester.

b. The mastic is applied to the substrate with a spatula to the thickness of the mold, leaving a smooth surface. The mold is removed and a 1" wide strip of airplane fabric is placed on the mastic surface. The fabric should be long enough to cover the length of the film at 180 degrees, and have enough left over to fit into the "Instron" jaws.

c. The mold is placed over the fabric and around the mastic film. Additional mastic is applied over the fabric surface inside the mold.

d. By means of a spatula or broadknife, apply slight pressure and tool and mastic until the fabric is about ½ the depth of the mastic and it is covered with a smooth film.

e. Remove the mold and allow the film to cure about seven days at room temperature and seven days in a forced air oven set at 190° F. Then re-condition one day at room temperature.

f. The cured specimens of compound are then cut along the outer edges of the fabric to the substrate.

g. The specimen is then placed on the "Instron" Tensile Tester and the cloth is pulled back over on itself at 180 degrees and fitted into the separation jaws.

h. The rate of separation of the jaws on the "Instron" Tester is maintained at two inches per minute, with a chart speed of one inch per minute. The values are recorded in pounds per inch.

Variations: Equipment (d)—Test Fabrics, Inc., Style 429 substituted for the Grade A airplane fabric.

Procedure (e)—The specimens were cured for 3 weeks at 23° C. and 50% relative humidity.

As shown in Table 9, on the aluminum substrate, the major mode of failure was adhesive failure where the caulk pulls cleanly away from the substrate. In general, all of the caulks in the same series of plasticizer yielded similar results. There were some slight differences from plasticizer to plasticizer, however.

On the glass substrate, all of the caulks performed similarly. The major mode of failure was a combination of adhesive and cohesive failure, where some of the caulk remains on the substrate and some remains on the laminate wire.

The wood substrate gave the best results. All of the caulks failed by the cohesive peak mode which indicates a strong caulk and good adhesion to the substrate. The trend in the wood series was that the higher the hydroxyl value, the easier the wire was delaminated from the caulk.

Although there was some variations in the results by changing the hydroxyl value of the plasticizer used, it is not believed that these differences do not render the plasticizer unsuitable.

e. Tensile Properties

The following tests were performed on the actual caulks made according to the formulations of Table 7, using the plasticizers of Table 1. All of the following tests were performed according to ASTM No. D-638 adopted for testing of caulks. The results of the following tests are shown in Table 9.

(i) Modulus Values: the modulus value at a specific elongation is an indication of the caulk hardness. A softer cured caulk will have a lower modulus value. The more efficient the plasticizer, the softer the cured caulk and therefore, the lower the modulus value. For this study, the modulus was evaluated at fifty percent elongation.

Little difference was seen in the modulus values within a series of plasticizer. Both the dipropylene glycol dibenzoate and dipropylene glycol dibenzoate/diethylene glycol 50/50 blend series had lower modulus values than the diethylene glycol dibenzoate series or Butyl Benzyl Phthalate. This would indicate that the efficiency of the plasticizer is not compromised by increasing the hydroxyl value.

(ii) Maximum Tensile: All of the caulks yielded prior to complete failure during the tensile testing. Since the tensile at break was essentially zero, the tensile strength was determined at break. The results indicate that caulks with the low hydroxyl plasticizers have lower but acceptable tensile strength. In all the series, the caulks with the low hydroxyl plasticizers had the lowest tensile strength. The dipropylene glycol dibenzoate/diethylene glycol dibenzoate had the lowest tensile strength of all of the caulks tested.

(iii) Elongation: The elongation at break was determined for all of the caulks tested. As would be expected, the elongation results were indicative of the tensile results. The trend was that the higher the tensile strength, the lower the elongation.

(iv) Shore A Hardness: The Shore A Hardness is a measure of a plasticizer's efficiency, like the modules value in nature. A softer cured caulk indicates better plasticizer efficiency. Increasing the hydroxyl value of the plasticizer resulted in a softer caulk. All of the caulks made with plasticizer that had higher hydroxyl values were softer than their control. With one exception, all of the benzoate caulks were softer than the Sanitizer 160 caulk. In each series of plasticizers, the medium and high hydroxyl plasticizer resulted in caulks with equal hardness. The hardness data is listed in Table 10, with all of the tests performed in accordance with ASTM D2240.

f. Cure Tests

The cure of a latex caulk is best evaluated by examining the tack free time, and cure through time. This data is presented in Table 11. The "cure through time" and "tack free" tests were performed according to tests designed by Rohm & Haas.

(i) Tack Free Time: Tack free time is a measure of the speed at which the caulk forms a skin, in other words, how fast the surface of the caulk drys. It is better for a caulk to form a skin that will allow painting as soon as possible.

The tack-free time test performed was as follows: A sample of compound is stored for 16 to 24 hours at standard conditions. A brass frame with inside dimensions 1½" wide× 5" long×¼" deep is centered on a 3"×6" plate of 16 to 24 gauge aluminum and filled with the conditioned compound. Excess compound is struck off with a flat spatula. A thin knife is then run along the inside edge of the frame to free the frame, and the frame is removed. Tack-free time is determined by placing a polyethylene strip approximately 2" wide×4" long×0.004" thick on the top surface of the compound as soon as it appears that the tackiness is gone. The assembly is then overlaid with a 30 gram brass block measuring approximately 1" wide×1⅝" long×⅛" thick. After 30 seconds, the weight is removed and the film is progressively withdrawn at right angles to the compound. The compound is considered tack-free if the film pulls away from the specimen without any compound adhering to it. Tack-free time is measured in minutes from the time the frame is removed from the specimen.

The data indicates that the general trend of the tack free time is that caulks having the low hydroxyl plasticizers had the shortest tack free time in the same series of plasticizers. The tack free time rarely increased by more than five minutes over the caulks having low hydroxyl plasticizers when the hydroxyl value of the plasticizer was increased. Five minutes was the interval between testing. All the caulks performed acceptably.

(ii) Cure Through Time: A Rohm & Haas cure-through procedure was employed. Aluminum Q panels (Type A, alloy 3003H14, 3"×9"×0.025") were used as the substrate. Two methods of judging cure-through were employed. The first method used attempted to judge complete cure by qualitatively estimating strength development. In the second method, the complete loss of liquid consistency was used as the judgement criteria for cure. The Rohm & Haas test is further described below.

A sample of compound is stored for 16 to 24 hours at standard conditions. A brass frame with inside dimensions 1½" wide by 5" long×¼" deep is centered on a 3"×6" plate of 16 to 24 gauge aluminum and filled with the conditioned compound. Excess compound is struck off with a flat spatula. A thin knife is then run along the inside edge of the frame to free the frame, and the frame is removed. The specimen is allowed to air-cure at standard conditions. Every 24 hours from the time of application, a section not less than ¼" in width is removed by cutting through the specimen from the top surface to the aluminum plate (parallel to the 1½ dimension of the specimen), and the amount of cure is observed with each cutting. The cure-through time is reported in days from the time the specimen is prepared.

The results indicate the hydroxyl value had no effect on the amount of time needed to achieve cure through. All of the caulks tested were cured through the quarter inch thickness in the same amount of time.

g. Low Temperature Flexibility—The procedure used was as follows.
1. Sample Preparation
   a. Equipment—Teflon frame—5"×1½"×⅛" inside dimensions; Spatula
   b. Materials—Caulks, Aluminum Q Panels—Type A Alloy 3003H14 3"×9"×0.025"
   c. Procedure
      1. Place the frame on the degreased Aluminum Q Panel (degreased with acetone) and trowel caulk into cavity.
      2. Level caulk to frame thickness with spatula.
      3. Run thin spatula along inside edge of the cavity to allow the removal of the frame. Remove the frame.
      4. Cure—One set is cured at 23° C. and 50% relative humidity for three weeks and the other set is cured at 70° C. for three weeks.
2. Low Temperature Flexibility Test
   a. Equipment
      Gardner Laboratories Mandrel Set Cold Box –26° C.
   b. Procedure
      1. Place caulks on aluminum panels (prepared as above) in the cold box and condition for four hours. Also, condition mandrel stand and one inch mandrel.
      2. Conduct test in the cold box. Place panel in the center of the mandrel, aluminum side down and bend 120 degrees in one second.
      3. Observe for cracking and adhesive failure. Record observation.

Low temperature flexibility is an important measure of a caulks durability. Two sets of caulk samples were prepared for this test. One set was cured at room temperature. The other set was cured at 70° C. All of the samples were cured for three weeks prior to testing. The high temperature curing is a good indication of plasticizer permanence, since some of the plasticizer could be lost from the caulk at the elevated temperature.

All of the samples tested passed the flexibility testing. There were no signs of cracking or delamination from the aluminum substrate in any of the twenty panels that were flexed.

These results indicate that all of the plasticizers are all very permanent under the conditions tested. Also the cured caulks are very durable.

EXAMPLE 3

Environmental Testing

Outdoor testing of caulks having the plasticizers of the present invention demonstrates the surprising and unexpected benefits of the present invention over the prior art.

Actual testing of caulks having the plasticizers of the present invention was performed by an independent facility in south Florida. Specifically, various caulks were applied to fences and analyzed for resistance to mold and mildew growth over prolonged periods of time. The results are shown in Table 12. As shown in this table, the caulks having plasticizers with high hydroxyl values had significantly more resistance to fungal growth than caulks having plasticizers with lower hydroxyl values.

List of Tables

| Table | Description |
|---|---|
| Table 1 | Plasticizer Identification and Hydroxyl Number for ASTM G-21 Tests |
| Table 2 | Results of ASTM 6-21 on Nutrient-Type Agar |
| Table 3 | Results of ASTM G-21 - Effect of Benzoic Acid content on Fungal Resistance |
| Table 4 | Plasticizer Identification and Hydroxyl Number for Caulk Testing |
| Table 5 | Viscosity Response Formula |
| Table 6 | Viscosity Response Data |
| Table 7 | Caulk Formula |
| Table 8 | Semco Gun Consistency Data |
| Table 9 | Caulk Peel Adhesion Data |
| Table 10 | Cured Caulk Tensile Data |
| Table 11 | Cure Through and Tack Free Time Data |
| Table 12 | Latex Caulk Exterior Exposure Data |

TABLE 1

Plasticizer Identification and Hydroxyl Number for ASTM G-21 Tests

| Plasticizer Type | Plasticizer Label | Hydroxyl Number |
|---|---|---|
| Dipropylene glycol dibenzoate | A | 44.6 |
| Dipropylene glycol dibenzoate | B | 27.6 |
| Dipropylene glycol dibenzoate | C | 12.7 |
| Dipropylene glycol dibenzoate and Diethylene glycol dibenzoate | D | 45.3 |
| Dipropylene glycol dibenzoate and Diethylene glycol dibenzoate | E | 27.9 |
| Dipropylene glycol dibenzoate and Diethylene glycol dibenzoate | F | 12.4 |
| Diethylene glycol dibenzoate | G | 12.1 |
| Diethylene glycol dibenzoate | H | 28.1 |
| Diethylene glycol dibenzoate | I | 46.6 |
| Butyl benzyl phthalate | J | 0 |

TABLE 2

Results of ASTM G-21 on Nutrient-Type Agar

| Plasticizer Label | Week 1 | Week 2 | Week 3 |
|---|---|---|---|
| A | 0 | 0 | 2 |
| B | 1 | 1 | 2 |
| C | 1 | 1 | 4 |
| D | 0 | 0 | 1 |
| E | 0 | 0 | 3 |
| F | 2 | 2 | 3 |
| G | 0 | 0 | 3 |
| H | 1 | 1 | 4 |
| I | 0 | 2 | 3 |
| J | 3 | 4 | 4 |
| Positive Control, no plasticizer | 3 | 4 | 4 |

TABLE 3

Results of ASTM G-21 Test - Effect of Benzoic Acid content on Fungal Resistance

| Plasticizer/Additive | 1** | 2 (Day 4) | 3 (Day 6) | 4 (Day 9) | 5 (Day 11) | 6 (Day 14) | 7 (Day 18) | 8 (Day 23) |
|---|---|---|---|---|---|---|---|---|
| DPGB | 0 | 1 | 2 | 3 | 4 | 4 | 4 | 4 |
| DPGB/BA* 0.2% | 0 | 1 | 2 | 3 | 4 | 4 | 4 | 4 |
| DPGB/BA 0.4% | 0 | 1 | 2 | 3 | 4 | 4 | 4 | 4 |
| DPGB/BA 0.8% | 1 | 1 | 2 | 3 | 3 | 4 | 4 | 4 |
| DPGB/BA 1.2% | 0 | 0 | 2 | 3 | 4 | 4 | 4 | 4 |

DPGB - Dipropylene glycol dibenzoate
*BA - benzoic acid
**First reading was made two days after inoculation.
(known fungicide)
Conclusion: Increased BA did not provide any antifungal resistance.

TABLE 4

PLASTICIZER IDENTIFICATION AND HYDROXYL NUMBER FOR CAULK TESTING

| Plasticizer Identification No. | Plasticizer Type | Hydroxyl Number |
|---|---|---|
| 1 | Dipropylene glycol benzoates (abbr. DPGB) | 101.7 |
| 2 | DPGB | 72.6 |
| 3 | DPGB | 12.7 |
| 4 | 50/50 Blend of Dipropylene glycol and Dietfiyiene glycol benzoates (abbr. "Blend") | 78.0 |
| 5 | 50/50 Blend | 55.1 |
| 6 | 50/50 Blend | 14.4 |
| 7 | Diethylene glycol benzoates (abbr. DEGB) | 58.4 |
| 8 | DEGB | 39.6 |
| 9 | DEGB | 12.1 |
| 10 | Butyl benzyl phthalate | 0 |

TABLE 5

VISCOSITY RESPONSE FORMULA

| INGREDIENTS | PARTS BY WEIGHT |
|---|---|
| Rhoplex ® 1785 | 100.0 |
| Triton ® X-405 | 2.3 |
| Plasticizer | 55.0 |
| Total | 157.3 |

TABLE 6

VISCOSITY RESPONSE DATA

| PLASTICIZER IN FORMULA | | ONE HOUR VISCOSITY, CPS | 24 HOUR VISCOSITY, CPS |
|---|---|---|---|
| TYPE | HYDROXYL NUMBER | | |
| NONE | | 430 | 400 |
| 1 | 101.7 | 93600 | 89200 |
| 2 | 72.6 | 90800 | 113600 |
| 3 | 12.7 | 119800 | 124400 |
| 4 | 78.0 | 73600 | 85000 |
| 5 | 55.1 | 97400 | 91800 |
| 6 | 14.4 | 117000 | 127600 |
| 7 | 58.4 | 83800 | 79800 |
| 8 | 39.6 | 91000 | 87600 |
| 9 | 12.1 | 79800 | 78400 |
| 10 | 0 | 141600 | 150400 |

MEASUREMENTS TAKEN WITH A BROOKFIELD LVT AT 3 RPM'S
READINGS TAKEN AFTER TEN REVOLUTIONS

TABLE 7

CAULK FORMULA

| INGREDIENTS | | PARTS BY WEIGHT |
|---|---|---|
| Rhoplex ® 1785 | (acrylic emulsion) | 925.0 |
| Water | | 2.6 |
| Ethylene Glycol | | 25.0 |
| Tamol ® 850 | (Anionic dispersant, sodium salt of polymeric carboxylic acid, made by Rohm & Haas Co.) | 2.6 |
| Potassium tripolyphosphate | | 2.6 |
| Plasticizer | | 254.0 |
| Varsol #1 | (tooling additive, mineral spirits, made by Exxon Co.) | 20.0 |
| Silane Z 6040 | (glycidoxypropyl trimethoxysilane made by Dow Coming, Midland MI) | 1.2 |
| Drikalite ® | (Calcium carbonate filler made by ECC International, Atlanta, GA) | 1250.0 |

TABLE 7-continued

CAULK FORMULA

| INGREDIENTS | | PARTS BY WEIGHT |
|---|---|---|
| Ti-pure ® R-901 | (whitening pigment, titanium dioxide made by E.I. DuPont de Nemons, Inc., Wilmington, DL) | 20.0 |
| Triton ® X-405 | (non-ionic surfactant, alkyl aryl polyether alcohol made by Rohm & Haas Co.) | 20.0 |
| $NH_3OH$ | | 5.0 |
| TOTAL | | 2528.0 |

TABLE 8

SEMCO GUN CONSISTENCY DATA
SEMCO GUN CONSISTENCY AT 23° C. AFTER (g/sec)

| Plasticizer In Caulk Type | Hydroxyl Number | Freeze/Thaw Pass/Fail | 1 Day RT | 7 Days RT | 28 Days RT | Ratio 28 RT/1 RT | 3 Cycles F/T | Ratio F/T to 7 RT | 28 Days AT 50° C. | Ratio 50° C./7 RT |
|---|---|---|---|---|---|---|---|---|---|---|
| 1 | 101.7 | PASS | 4 | 3 | 13 | 3.3 | 11 | 3.7 | 15 | 5.0 |
| 2 | 72.6 | PASS | 15 | 15 | 10 | 0.7 | 14 | 0.9 | 14 | 0.9 |
| 3 | 12.7 | PASS | 10 | 12 | 11 | 1.1 | 11 | 0.9 | 8 | 0.9 |
| 4 | 78.0 | PASS | 14 | 13 | 13 | 0.9 | 19 | 1.5 | 17 | 1.3 |
| 5 | 55.1 | PASS | 21 | 19 | 14 | 0.7 | 31 | 1.6 | 18 | 0.9 |
| 6 | 12.4 | PASS | 16 | 15 | 14 | 0.9 | 13 | 0.9 | 19 | 1.3 |
| 7 | 58.4 | PASS | 12 | 5 | 8 | 0.7 | 8 | 1.6 | 9 | 1.8 |
| 8 | 39.6 | PASS | 17 | 15 | 13 | 0.8 | 14 | 0.9 | 12 | 0.8 |
| 9 | 12.1 | FAIL | 10 | 7 | 8 | 0.8 | FAIL | — | 8 | 1.1 |
| 10 | 0 | PASS | 21 | 19 | 9 | 0.4 | 7 | 0.4 | 9 | 0.4 |

TABLE 9

CAULK PEEL ADHESION DATA

| PLASTICIZER IN CAULK | | ALUMINUM 180° PEEL | | | GLASS 180° PEEL | | | WOOD 180° PEEL | | |
|---|---|---|---|---|---|---|---|---|---|---|
| Type | Hydroxyl Number | TYPE OF FAILURE MAJOR | AVERAGE | lb/in. STD. DEV. | TYPE OF FAILURE MAJOR | AVERAGE | lb/in. STD. DEV. | TYPE OF FAILURE MAJOR | AVERAGE | lb/in. STD. DEV. |
| 1 | 101.7 | A | 8.8 | 0.4 | A/C | 10.1 | 0.5 | CP | 11.5 | 0.7 |
| 2 | 72.6 | A | 9.2 | 0.9 | A/C | 10.7 | 0.4 | CP | 12.1 | 0.4 |
| 3 | 12.7 | A | 9.7 | 0.4 | A/C | 10.7 | 0.8 | CP | 13.7 | 0.4 |
| 4 | 78.0 | A | 7.5 | 0.1 | A/C | 10.0 | 0.5 | CP | 11.4 | 0.5 |
| 5 | 55.1 | A | 7.8 | 0.4 | A/C | 10.7 | 0.8 | CP | 11.5 | 0.4 |
| 6 | 14.4 | A | 9.8 | 1.8 | A/C | 11.3 | 0.7 | CP | 11.7 | 0.8 |
| 7 | 58.4 | A | 8.2 | 0.6 | A/C | 11.3 | 0.5 | CP | 12.5 | 0.4 |
| 8 | 39.6 | A | 7.6 | 0.4 | A/C | 11.5 | 0.6 | CP | 13.0 | 0.6 |
| 9 | 12.1 | A | 7.8 | 0.4 | A/C | 12.6 | 0.5 | CP | 13.1 | 0.5 |
| 10 | 0 | A | 9.5 | 0.9 | A/C | 13.1 | 0.4 | CP | 13.4 | 0.7 |

MAJOR MODE OF FAILURE -
A = ADHESIVE,
C = COHESIVE,
CP = COHESIVE PEAK

TABLE 10

CURED CAULK TENSILE DATA

| PLASTICIZER IN CAULK | | 50% MODULUS | | MAXIMUM TENSILE | | ELONGATION AT BREAK | | SHORE |
|---|---|---|---|---|---|---|---|---|
| TYPE | Hydroxyl Number | PSI | STD. DEV. | PSI | STD. DEV. | PERCENT | STD. DEV. | A |
| 1 | 101.7 | 7 | 1 | 35 | 2 | 720 | 30 | 24 |
| 2 | 72.6 | 7 | 2 | 37 | 4 | 630 | 40 | 24 |
| 3 | 12.7 | 6 | 1 | 33 | 3 | 690 | 40 | 27 |
| 4 | 78.0 | 7 | 1 | 37 | 2 | 650 | 20 | 20 |
| 5 | 55.1 | 8 | 1 | 38 | 4 | 660 | 20 | 20 |
| 6 | 12.4 | 8 | 1 | 30 | 3 | 680 | 20 | 23 |
| 7 | 58.4 | 10 | 1 | 46 | 4 | 660 | 50 | 28 |
| 8 | 39.6 | 11 | 1 | 49 | 7 | 640 | 30 | 28 |
| 9 | 12.1 | 13 | 1 | 45 | 3 | 610 | 60 | 40 |
| 10 | 0 | 11 | 1 | 41 | 2 | 650 | 20 | 35 |

TABLE 11

CURE THROUGH AND TACK FREE TIME DATA

| PLASTICIZER IN CAULK | | CURE THROUGH TIME (DAYS) | TACK FREE TIME (MIN). |
|---|---|---|---|
| TYPE | HYDROXYL NUMBER | | |
| 1 | 10.17 | 9 | 45 |
| 2 | 72.6 | 9 | 45 |
| 3 | 12.7 | 9 | 40 |
| 4 | 78.0 | 9 | 40 |
| 5 | 55.1 | 9 | 50 |
| 6 | 12.4 | 9 | 45 |
| 7 | 58.4 | 9 | 40 |
| 8 | 39.6 | 9 | 40 |
| 9 | 12.1 | 9 | 35 |
| 10 | 0 | 9 | 40 |

TABLE 12

Latex Caulk Exterior 90 Degree Northern Exposure Data
South Florida Fence

| PLASTICIZER Exposure Time | DPGDB, 101.7 OH | DPGDB, 72.6 OH | DPGDB, 12.7 OH | Blend, 78.0 OH | Blend, 55.1 OH | Blend, 14.4 OH | DEGDB, 58.4 OH | DEGDB, 39.6 OH | DEGDB, 12.1 OH | BSP |
|---|---|---|---|---|---|---|---|---|---|---|
| 1 Month | 10 | 10 | 10 | 10 | 10 | 10 | 10 | 10 | 10 | 10 |
| 2 Months | 10 | 10 | 10 | 10 | 10 | 10 | 10 | 10 | 10 | 10 |
| 3 Months | 10 | 10 | 10 | 10 | 10 | 10 | 10 | 10 | 10 | 10 |
| 4 Months | 10 | 10 | 10 | 10 | 10 | 10 | 10 | 10 | 10 | 10 |
| 5 Months | 10 | 10 | 9.5 | 10 | 9.5 | 10 | 10 | 9.5 | 9 | 8 |
| 6 Months | 10 | 10 | 9.5 | 10 | 9.5 | 9 | 10 | 9.5 | 9 | 8 |
| 7 Months | 9 | 8.5 | 8 | 9 | 9 | 8 | 9 | 9 | 9 | 8 |
| 8 Months | 9 | 8 | 7 | 9 | 9 | 8 | 9 | 9 | 8 | 8 |
| 9 Months | 8 | 7 | 5 | 8 | 7 | 6 | 8 | 8 | 6 | 5 |
| 10 Months | 7 | 7 | 4 | 8 | 7 | 4 | 8 | 7 | 6 | 5 |
| 11 Months | 7 | 7 | 4 | 7 | 7 | 6 | 7 | 7 | 6 | 4 |
| 12 Months | 6 | 6 | 4 | 6.5 | 6 | 4 | 6.5 | 6.5 | 5 | 4 |

Rating of 10 is the best rating. A rating below 8 indicates failure.
DPGDB is dipropylene glycol dibenzoate. DEGDB is diethylene dibenzoate.
Blend is a one to one blend of the above dibenzoates.

Those of skill in the art will recognize that the plasticizers of the present invention can be used in other applications, including but not limited to adhesives, latex coatings (e.g. acrylic, vinyl acrylic, vinyl acetate, etc.) and floor polishes. It is expected that the plasticizers of the present invention will exhibit resistance to fungal growth in these other applications and posses coalescing characteristics as well.

The foregoing detailed description of the invention has been made in general terms and with respect to several preferred embodiments. Many of the preferred embodiments stated herein may be varied by persons skilled in the art without departing from the spirit and scope of the present invention as set forth in the following claims and equivalents.

What is claimed is:

1. A plasticizer comprising dipropylene glycol dibenzoate, the improvement comprising the addition of dipropylene glycol monobenzoate, whereby the plasticizer is resistant to fungal growth.

2. A plasticizer comprising diethylene glycol dibenzoate, the improvement comprising the addition of diethylene glycol monobenzoate, whereby the plasticizer is resistant to fungal growth.

3. A plasticizer comprising dipropylene glycol dibenzoate and diethylene glycol dibenzoate, the improvement comprising the addition of dipropylene glycol monobenzoate and/or diethylene glycol monobenzoate, whereby the plasticizer is resistant to fungal growth.

4. A latex caulk comprising the plasticizer of claim 1.
5. A latex caulk comprising the plasticizer of claim 2.
6. A latex caulk comprising the plasticizer of claim 3.
7. An adhesive comprising the plasticizer of claim 1.
8. An adhesive comprising the plasticizer of claim 2.
9. An adhesive comprising the plasticizer of claim 3.
10. A floor polish comprising the plasticizer of claim 1.
11. A floor polish comprising the plasticizer of claim 2.
12. A floor polish comprising the plasticizer of claim 3.

* * * * *